United States Patent [19]

Remy et al.

[11] 4,021,561
[45] May 3, 1977

[54] TRIFLUOROMETHYLTHIO- AND TRIFLUOROMETHYLSULFONYL-THIOXANTHEN-9-YLIDENEPIPERIDINES

[75] Inventors: David C. Remy, North Wales; Susan F. Britcher, Norristown, both of Pa.

[73] Assignee: Merck & Co., Inc., Rahway, N.J.

[22] Filed: Dec. 22, 1975

[21] Appl. No.: 642,866

[52] U.S. Cl. .......................... 424/267; 260/293.57
[51] Int. Cl.² ...................... C07D 409/04
[58] Field of Search ............... 260/293.57; 424/267

[56] References Cited

UNITED STATES PATENTS 3,275,640    9/1966    Engelhardt et al. ............ 260/293.4

OTHER PUBLICATIONS

Engelhardt et al., J. Med. Chem. 8, pp. 829–835, (1965).
Kaiser et al., J. Med. Chem. 17, pp. 57–62, (1974).

*Primary Examiner*—G. Thomas Todd
*Attorney, Agent, or Firm*—William H. Nicholson; Harry E. Westlake, Jr.

[57] ABSTRACT

1-Methyl-4-[2-(trifluoromethylthio)thioxanthen-9-ylidene]piperidine and the corresponding 2-trifluoromethylsulfonyl compound are antipsychotic agents. They are prepared by dehydration of the corresponding 9-hydroxy-9-piperidyl compounds.

8 Claims, No Drawings

TRIFLUOROMETHYLTHIO- AND TRIFLUOROMETHYLSULFONYL-THIOXAN-THEN-9-YLIDENEPIPERIDINES

BACKGROUND OF THE INVENTION

This invention is concerned with a compound of structural formula:

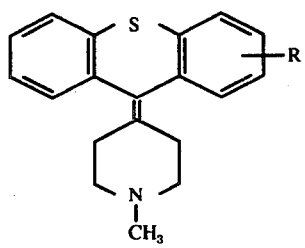

or pharmaceutically acceptable salts thereof, wherein R is $-SCF_3$ or $-SO_2CF_3$.

It is also concerned with a process for preparing the novel compounds, pharmaceutical compositions comprising the novel compounds as active ingredients, and a method of treating psychoses by administration of the novel compounds to a psychotic patient. Thioxanthenylidine piperidines are known in the art and known to have pharmacological activity. For example, the parent compound and the 2-chloro analog were described as antiserotonin and antihistaminic agents by Engelhardt et al. in *J. Med. Chem.*, 8, 829 (1965). Similar activities are described for the halo, alkyl, perfluoroalkyl, and alkoxy analogs by Engelhardt et al., in U.S. Pat. No. 3,275,640. Kaiser et al., in *J. Med. Chem.*, 17, 57 (1974) describes the chloro and trifluoromethyl derivatives as neuroleptic agents as measured by their ability to cause ptosis, catalepsy and decreased motor activity in rats.

Detailed Description of the Invention

The novel compounds of this invention have structural formula:

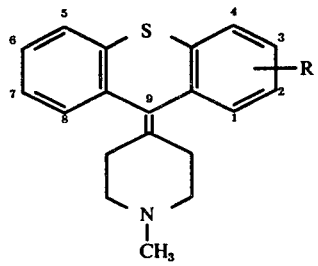

or pharmaceutically acceptable salts thereof wherein R is $-SCF_3$ or $-SO_2CF_3$.

A preferred embodiment thereof is the compound wherein R is in the 2-position. An even more preferred embodiment is that wherein R is in the 2-position and represents $-SO_2CF_3$.

The pharmaceutically acceptable salts contemplated to be within the scope of this invention are those prepared from inorganic and organic acids known in the art to yield pharmaceutically acceptable salts such as phosphoric, hydrochloric, hydrobromic, sulfuric, maleic, pamoic, citric, pyruvic, naphthalenesulphonic, isethionic, fumaric acids or the like.

The novel process of this invention comprises dehydration of the 9-hydroxy-9-piperidyl compound represented as follows:

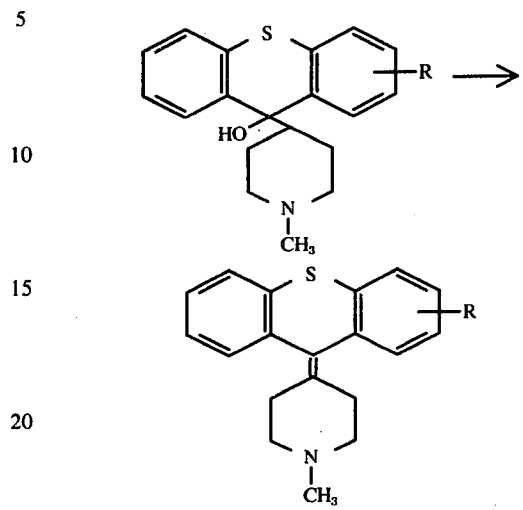

The reaction is conducted by heating at 50° C. to reflux temperature for 1–5 hours a solution of the 9-hydroxy starting material in a mixture of 1 part of trifluoroacetic acid and 1–4 parts trifluoroacetic anhydride.

The preparation of the 9-hydroxy starting materials are fully described in the Examples herein.

The novel method of treatment of this invention comprises the administration of a novel compound to a psychotic patient. The route of administration can be oral, rectal, intravenous, intramuscular, or subcutaneous. Doses of 2 to 200 mg./kg./day and preferably of 5 to 50 mg./kg./day of active ingredient are generally adequate, and if preferred, can be administered in divided doses given two to four times daily.

It is to be noted that the precise unit dosage form and dosage level depend upon the case history of the individual being treated and, consequently, are left to the discretion of the therapist.

Pharmaceutical compositions comprising a novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous, intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above-described pharmaceutical compositions may be from 1 to 400 mg., and preferably from 5 to 250 mg.

EXAMPLE 1

1-Methyl-4-[2-(trifluoromethylthio)thioxanthen-9-ylidene] piperidine

Step A:

Preparation of 2-(trifluoromethylthio)thioxanthen9-one

A mixture of 13.0 g. (0.0446 mol) of 2-bromothioxanthen-9-one, 30.87 g. (0.0766 mol) of bis-(trifluoromethylthio)mercury, 20.36 g. (0.32 mol) of copper powder, 7 ml. of pyridine and 70 ml. of quinoline is stirred at 170°–190° for 20 hours. The solution is cooled and diluted with 200 ml. of 6N hydrochloric acid and 200 ml. of benzene. After stirring vigorously, the mixture is filtered through Filter-Cel using benzene to wash the filter cake. The aqueous acid phase is removed and the benzene phase is washed with 200 ml. of 3N hydrochloric acid and four 250 ml. portions of water. After drying over magnesium sulfate, the solution is filtered and the benzene is removed. The residue is dissolved in a small amount of benzene and chromatographed on a silica gel column (2 × 30 inches) packed in benzene. The product is eluted with benzene to give 5.90 g. of material, which, after recrystallization from methanol gives 5.24 g. of 2-(trifluoromethylthio)-thioxanthen-9-one, m.p. 126°–127°.

Step B:

Preparation of 1-methyl-4-(2-trifluoromethylthio-9-hydroxythioxanthen-9-yl)piperidine To an ice cooled solution of 5.10 g. (0.0163 mol) of 2-(trifluoromethylthio)thioxanthen-9-one in 60 ml. of dry tetrahydrofuran is added dropwise 25 ml. of 0.72 M 1-methyl-4-piperidylmagnesium chloride in tetrahydrofuran. After the addition is complete, the solution is stirred at room temperature for 1 hour. The tetrahydrofuran is removed on a rotary evaporator. The red-oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of boiling benzene. The benzene phases are combined and evaporated to dryness. The residue, which crystallizes when triturated with acetonitrile, is removed by filtration and washed with acetonitrile to give 3.29 g. of 1-methyl-4-(2-trifluoromethylthio-9-hydroxythioxanthen-9-yl)piperidine.

Step C:

Preparation of 1-methyl-4-[2-(trifluoromethylthio)thioxanthen-9-ylidene]piperidine A solution of 3.29 g. of 1-methyl-4-(2-trifluoromethylthio-9-hydroxythioxanthen-9yl)piperidine in 15 ml. of trifluoroacetic anhydride and 30 ml. of trifluoroacetic acid is stirred and refluxed for 2.5 hours. The solution is evaporated to dryness. The residue is dissolved in benzene and is washed with 10% sodium hydroxide to make the free base form. The benzene is washed with water, dried over magnesium sulfate, filtered, and the benzene is removed on a rotary evaporator. The residue is recrystallized from acetonitrile to give 1-methyl-4-[2-(trifluoromethylthio)thioxanthen-9-ylidene]piperidine, m.p. 104°–106° C.

EXAMPLE 2

1-Methyl-4-[2-(trifluoromethylsulfonyl)thioxanthen9-ylidene]-piperidine

Step A:

Preparation of 2-(4-trifluoromethylsulfonylphenylthio)benzoic acid

A solution of 6.17 g. (0.040 mol) of thiosalicylic acid, 3.2 g. (0.08 mol) of sodium hydroxide, and 9.28 g. (0.032 mol) of 4-bromophenyl trifluoromethyl sulfone in 130 ml. of absolute ethanol and 15 ml. of water is stirred and refluxed for 24 hours. The solution is evaporated to dryness and the residue is dissolved in 300 ml. of water. After being extracted with benzene, the alkaline aqueous phase is acidified by the dropwise addition of concentrated hydrochloric acid. The granular precipitate that forms is removed by filtration and washed with water. The material is air dried. The solid is stirred with 100 ml. of benzene at 60° for 10 minutes, filtered, and the undissolved solid is washed with two 100 ml. portions of benzene. The combined benzene filtrate and washings are evaporated to give 5.4 gm. of 2-(4-trifluoromethylsulfonylphenylthio)-benzoic acid.

Step B:

Preparation of 2-(trifluoromethylsulfonyl)-thioxanthen-9-one

A solution of 7.6 g. (0.021 mol) of 2-(4-trifluoromethylsulfonylphenylthio)benzoic acid in 40 ml. of concentrated sulfuric acid is stirred and heated on a steam bath for 1.5 hours. After cooling to room temperature, the solution is slowly poured onto 400 g. of crushed ice. The oil that precipitates is extracted with three 150 ml. portions of an ether-benzene mixture. The combined organic extracts are washed four times with water and three times with dilute sodium bicabonate solution. The ether-benzene layer is dried over magnesium sulfate, filtered, and evaporated to dryness on a rotary evaporator. The pale yellow solid obtained is recrystalized from acetonitrile to give 2-(trifluoromethylsulfonyl)thioxanthen-9-one, m.p. 163°–164.5°.

Step C:

Preparation of 1-methyl-4-(2-trifluoromethylsulfonyl-9-hydroxythioxanthen-9-yl)piperidine To an ice cooled solution of 2.42 g. (0.007 mol) of 2-(trifluoromethylsulfonyl)thioxanthen-9-one in 25 ml. of dry tetrahydrofuran is added dropwise 15 ml. of 0.81M 1-methyl-4-piperidylmagnesium chloride is tetrahydrofuran. The solution is stirred overnight at room temperature and then the tetrahydrofuran is removed on a rotary evaporator. The red-oily residue that remains is dissolved in 100 ml. of benzene and water is added dropwise to give a clear benzene supernatant and a red gelatinous aqueous phase. The mixture is filtered and the residual solid is washed five times with boiling benzene. The combined filtrate and washings are washed with dilute ammonium chloride solution, two times with saturated sodium bicarbonate, and two times with water. The benzene phase is dried over sodium sulfate, filtered, and the benzene removed on a rotary evaporator. The residue, which crystallizes when triturated with acetonitrile, is removed by filtration and washed with ice cold acetonitrile to give 1.63 g. of 1-methyl-4-(2-trifluoromethylsulfonyl-9-hydroxy-thioxanthen9-yl)piperidine, m.p. 211°–216° C.

Step D:

Preparation of 1-methyl-4-[2-(trifluoromethylsulfonyl)thioxanthen-9-ylidene]piperidine A solution of 1.63 g. (0.00369 mol) of 1-methyl-4-(2-trifluoromethylsulfonyl-9-hydroxy-thioxanthen-9-yl) piperidine in 12 ml. of trifluoroacetic acid and 4 ml. of trifluoroacetic anhydride is stirred and refluxed for 3 hours. The solution is evaporated to dryness and the residue is partitioned between dilute sodium hydroxide and benzene-ether (1:1). The basic aqueous phase is extracted two more times with benzene-ether (1:1). The combined benzene-ether phases are washed with saturated sodium bicarbonate, three times with water, and dried over magnesium sulfate. The solution is filtered and the solvent is removed on a rotary evaporator. Trituration of the residue induces crystallization. The material is collected by filtration, washed with acetonitrile and dried at 77° C. in vacuo to give 1.05 g. of 1-methyl-4-(2-[trifluoromethylsulfonyl]thioxanthen-9-ylidene)piperidine, m.p. 125°–128° C.

EXAMPLE 3

Pharmaceutical Compositions

A typical tablet containing 100 mg. of active ingredient per tablet is prepared by mixing together with the active ingredient calcium phosphate, lactose and starch in the amounts shown in the table below. After these ingredients are thoroughly mixed, the appropriate amount of magnesium stearate is added and the dry mixture blended for an additional 3 minutes. This mixture is then compressed into tablets.

Tablet Formula

| Ingredient | Mg. per Tablet |
| --- | --- |
| 1-methyl-4-[2-(trifluoromethylsulfonyl)thioxanthen-9-ylidene]piperidine | 100 mg. |
| Calcium phosphate | 52 mg. |
| Lactose | 60 mg. |
| Starch | 10 mg. |
| Magnesium stearate | 1 mg. |

Similarly prepared are tablets comprising 1-methyl-4-[2-(trifluoromethylthio)thioxanthen-9-ylidene]-piperidine as active ingredient.

What is claimed is:

1. A pharmaceutical composition in unit dosage form comprising a carrier and an effective amount of a compound of structural formula:

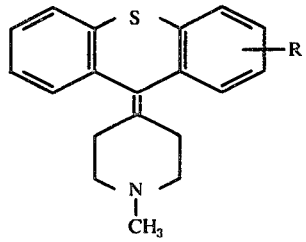

or pharmaceutically acceptable salt thereof, wherein R is $-SCF_3$ or $-SO_2CF_3$.

2. The pharmaceutical composition of claim 1, wherein the compound has structural formula:

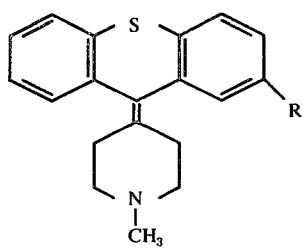

or pharmaceutically acceptable salt thereof.

3. A method of treating psychoses which comprises the administration to a patient in need of such treatment an effective amount of a compound of structural formula:

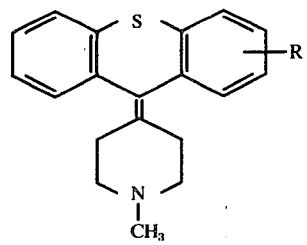

or pharmaceutically acceptable salt thereof, wherein R is $-SCF_3$ or $-SO_2CF_3$.

4. The method of claim 3, herein the compound has structural formula:

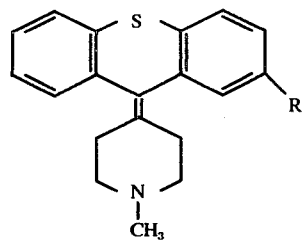

or pharmaceutically acceptable salt thereof.

5. A compound of structural formula:

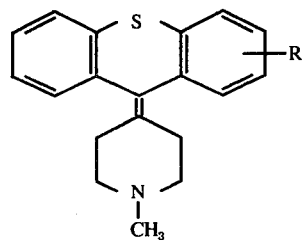

or pharmaceutically acceptable salts thereof wherein R is $-SCF_3$ or $-SO_2CF_3$.

6. The compound of claim 5 of structural formula:

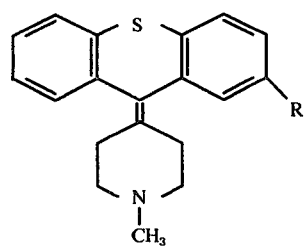

or pharmaceutically acceptable salt thereof.

7. The compound of claim 6, wherein R is $-SO_2CF_3$.

8. The compound of claim 6, wherein R is $SCF_3$.

* * * * *